(12) United States Patent
Trieu et al.

(10) Patent No.: US 9,795,771 B2
(45) Date of Patent: Oct. 24, 2017

(54) EXPANDABLE SPINAL ACCESS INSTRUMENTS AND METHODS OF USE

(75) Inventors: Hai H. Trieu, Cordova, TN (US); Sachin P. Budhabhatti, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 629 days.

(21) Appl. No.: 12/907,199

(22) Filed: Oct. 19, 2010

(65) Prior Publication Data
US 2012/0095296 A1    Apr. 19, 2012

(51) Int. Cl.
A61B 1/32 (2006.01)
A61M 29/02 (2006.01)

(52) U.S. Cl.
CPC .................. *A61M 29/02* (2013.01)

(58) Field of Classification Search
CPC ...................................................... A61M 29/02
USPC ........................... 606/86 A, 99; 600/206, 208
See application file for complete search history.

(56) References Cited

U.S. PATENT DOCUMENTS

| | | | |
|---|---|---|---|
| 3,789,852 A | 2/1974 | Kim et al. | |
| 4,545,374 A * | 10/1985 | Jacobson | 600/210 |
| 4,573,448 A * | 3/1986 | Kambin | 606/170 |
| 4,899,729 A * | 2/1990 | Gill | A61M 29/02 |
| | | | 606/198 |
| 4,921,479 A * | 5/1990 | Grayzel | 604/509 |
| 5,139,511 A * | 8/1992 | Gill et al. | 606/198 |
| 5,176,659 A * | 1/1993 | Mancini | A61M 25/0023 |
| | | | 604/164.1 |
| 5,183,464 A * | 2/1993 | Dubrul et al. | 606/198 |
| 5,318,588 A | 6/1994 | Horzewski et al. | |
| 5,447,503 A * | 9/1995 | Miller | 604/528 |
| 5,577,993 A * | 11/1996 | Zhu et al. | 600/204 |
| 5,792,044 A | 8/1998 | Foley et al. | |
| 5,824,054 A * | 10/1998 | Khosravi | A61F 2/92 |
| | | | 606/191 |
| 5,976,146 A * | 11/1999 | Ogawa et al. | 606/86 R |
| 6,338,730 B1 * | 1/2002 | Bonutti et al. | 604/509 |
| 6,494,860 B2 * | 12/2002 | Rocamora et al. | 604/43 |
| 7,063,725 B2 | 6/2006 | Foley | |
| 7,182,729 B2 | 2/2007 | Abdelgany et al. | |
| 7,261,688 B2 | 8/2007 | Smith et al. | |
| 7,534,250 B2 * | 5/2009 | Schaeffer et al. | 606/191 |
| 7,594,888 B2 | 9/2009 | Raymond et al. | |
| 7,699,864 B2 * | 4/2010 | Kick et al. | 606/198 |
| 2001/0011170 A1 | 8/2001 | Davison et al. | |
| 2001/0012950 A1 * | 8/2001 | Nishtala | A61M 25/0662 |
| | | | 606/198 |

(Continued)

OTHER PUBLICATIONS

Medtronic Direct Lateral Interbody Fusion DLIF Surgical Technique, Michelson Technology at Work, 40 pages, Copyright 2009 Medtronic Sofamor Danek USA, Inc.

*Primary Examiner* — Jan Christopher Merene
*Assistant Examiner* — Atiya Mahmud (57) ABSTRACT

A system for use in percutaneous surgical procedures includes a dilator with an expandable sleeve positioned around its outer surface that accepts one or more additional dilators or retractors between the sleeve and the dilator to form an access port to a surgical site in a patient. The system can be used in spinal surgical procedures and the sleeve and one or more additional components of the system can be radiolucent and disposable after use.

20 Claims, 10 Drawing Sheets

(56) References Cited

U.S. PATENT DOCUMENTS

| | | | |
|---|---|---|---|
| 2001/0012959 A1* | 8/2001 | Blaeser | A61F 2/958 623/1.11 |
| 2002/0032406 A1* | 3/2002 | Kusleika | 604/101.02 |
| 2006/0217754 A1 | 9/2006 | Boehm, Jr. et al. | |
| 2007/0032703 A1 | 2/2007 | Sankaran et al. | |
| 2008/0195146 A1 | 8/2008 | Wardle | |
| 2008/0200943 A1 | 8/2008 | Barker et al. | |
| 2009/0024203 A1* | 1/2009 | Hestad et al. | 623/1.15 |
| 2010/0145267 A1 | 6/2010 | Bishop et al. | |

* cited by examiner

EXPANDABLE SPINAL ACCESS INSTRUMENTS AND METHODS OF USE

BACKGROUND

The present application relates to systems and methods for performing surgery in a patient, and more particularly, but not exclusively, relates to systems and methods that employ instruments for accessing the spinal column and other locations within the body of a patient.

Traditional surgical procedures for pathologies located within the body involve extensive and lengthy cutting, removing, and or repositioning of skin and tissue surrounding the surgical site in order for the surgeon to access the surgical site. This type of approach may cause trauma, damage, and scarring to the tissue, and also presents risks that the tissue will become infected and that a long recovery time will be required after surgery for the tissue to heal. In some cases, these invasive procedures lead to permanent scarring and pain that can be more severe than the pain leading to the surgical intervention.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. Current techniques for minimally invasive surgery can involve prolonged tissue retraction and require advancing instruments into the body directly against tissue to increase the size of the access portal before an appropriately sized access portal to the surgical site is provided. These aspects of current techniques can lead to greater tissue morbidity and increased complexity and duration of the surgical procedure. Thus, there remains a need for further improvements in the devices, instruments, assemblies, apparatuses, systems and methods for performing minimally invasive and other surgical techniques.

SUMMARY

In one form, a system for use in percutaneous surgical procedures includes a dilator with an expandable sleeve around its outer surface that accepts one or more additional dilators or retractors between the dilator and the sleeve to form increase the size of and/or form an access port to a surgical site in a patient. In another form, a system for use in surgical procedures includes a disposable, radiolucent access sleeve that defines a working channel to the surgical site. In one aspect of either of these forms, an interbody spinal implant that is deliverable to the surgical site through the access port.

In another form, a surgical method includes inserting a guidewire into a patient; inserting a first dilator having an expandable sleeve attached thereto over the guidewire; inserting a second dilator larger in diameter than the first dilator between the first dilator and the expandable sleeve; continue insertion of dilators of increasing size until the access portal is of desired size. In one aspect of the method, a retractor is positioned between the last inserted dilator and the expandable sleeve, and the dilators removed to form an access port through the retractor to the surgical site. In a further aspect of the method, the retractor is disposable. The expandable sleeve and/or retractor can be made from a radiolucent material to facilitate imaging of the access portal and surgical site during the procedure.

The expandable sleeve described herein protects tissue along the access portal from possible cutting, pinching or other trauma during insertion of the dilators and/or retractor to the surgical site. The expandable sleeve can be of any suitable configuration or materials. Specific examples of expandable sleeves include a roll of thin material, coiled material, elastic tubing, and stretchable tubing with lubricated inner surface. The expandable sleeve and/or retractor can be made to be less expensive the conventional metal dilators and retractors so that disposal after the surgical procedure is feasible. In addition, the expandable sleeves can be provided with an anti-microbial coating to reduce the potential for infections that may result due to the surgery.

In still another form, there is provided a dilator including an elongate body extending between a proximal end and a distal end and including an expandable sleeve with an inner channel expandable from a first, unexpanded configuration. The dilator is located in the inner channel of the expandable sleeve so that the assembly can be positioned in the first configuration at a location adjacent to a surgical site. The inner channel of the sleeve is expanded from the first, unexpanded configuration with one or more additional dilators and/or retractors that are inserted in and distally advanced between the expandable sleeve and the previously inserted dilator toward the surgical site.

Another embodiment of the present application is a unique system for surgery in a patient. An additional embodiment of the present application is a unique dilator and outer sleeve combination where the sleeve includes a dynamically expandable inner channel. Other embodiments include unique methods, systems, devices, kits, assemblies, equipment, and/or apparatus for use in connection with percutaneous surgical procedures. However, in other embodiments, different forms and applications are envisioned.

Further embodiments, forms, features, aspects, benefits, objects and advantages of the present application shall become apparent from the detailed description and figures provided herewith.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments, systems, apparatuses, assemblies and methods for performing surgery, including spinal surgeries that include one or more techniques such as laminotomy, laminectomy, foramenotomy, facetectomy, discectomy, interbody fusion, spinal nucleus or disc replacement, and implant insertion including interbody implants and bone engaging fasteners, for example, are provided. The surgery is performed through an access portal, channel or passageway through skin and/or tissue of the patient protected by an expandable sleeve. In one form, viewing of the surgical site at the working end of the sleeve can be accomplished with naked eye visualization, microscopic viewing devices, loupes, viewing instruments mounted on the cannula, positioned over the cannula, positioned in other portals in the body, and/or through a viewing system such as lateral fluoroscopy. The sleeve is expandable in situ to increase the size of the access portal to facilitate access to the working space at the distal end of the sleeve while minimizing trauma to tissue surrounding the sleeve, and to protect tissue along the access portal as instruments for expanding the access portal are inserted into the patient. The sleeve can be used with any surgical approach to the spine, including anterior, posterior, posterior mid-line, lateral, postero-lateral, and/or antero-lateral approaches, and in other regions besides the spine.

In one embodiment, a system for percutaneous surgical procedures includes a sleeve having an elongate body extending along a longitudinal axis between a proximal end and a distal end and including an inner channel dynamically expandable from a first, unexpanded configuration by insertion of one or more dilators and retractors in the inner channel. The system also includes a device that includes a dilator and an expandable sleeve around the dilator so that the sleeve is larger than the dilator in the first configuration and the sleeve is expandable from the first configuration as a second dilator or retractor is positioned between the dilator and the sleeve. When the desired size access port is achieved by sequential dilation, the last inserted dilator or retractor remains in the patient with the sleeve extending therearound, and the previously inserted dilators are removed. In one aspect of this form, an interbody spinal implant that is deliverable to a surgical site through the access port formed by the last inserted dilator or retractor. The sleeve protects tissue along the access portal from the insertion of the dilators and retractors one over the other. It should be appreciated that alternative forms, aspects, configurations, arrangements and methods are contemplated with respect to the subject matter disclosed and described herein.

Figure 1:
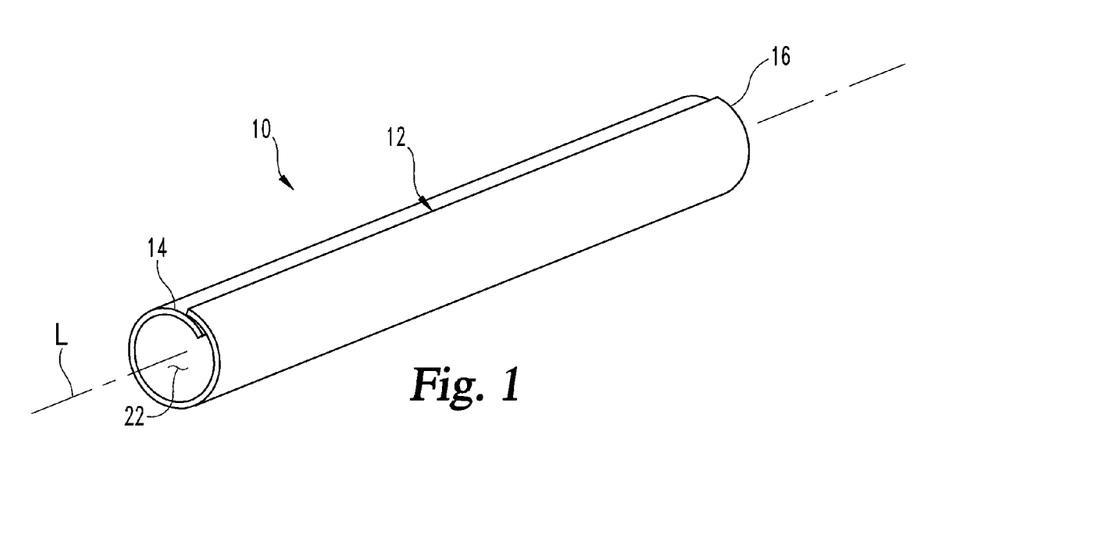
FIG. 1 is a perspective view of one embodiment of a sleeve including an expandable inner channel.

One embodiment sleeve 10 is illustrated in a perspective view in FIG. 1. Sleeve 10 includes an elongate body 12 extending along longitudinal axis L between a proximal end 14 and a distal end 16. Elongate body 12 generally includes a length between proximal end 14 and distal end 16 that facilitates positioning of proximal end 14 above the skin of a patient when distal end 16 is positioned adjacent to the targeted surgical site. Elongate body 12 is at least partially spirally wound or coiled around longitudinal axis L from proximal end 14 to distal end 16 and includes a dynamically expandable inner channel 22 which, in the form illustrated in FIG. 1, is provided in an unexpanded configuration. Inner channel 22 extends between and opens at proximal end 14 and distal end 16 and, in the unexpanded configuration, is generally uniformly sized and shaped between proximal end 14 and distal end 16. However, it is also contemplated that inner channel 22 could be non-uniformly sized and shaped between proximal end 14 and distal end 16 in the unexpanded configuration. In addition, it should be appreciated that the size and shape of inner channel 22 in the unexpanded configuration will depend on how tightly elongate body 12 is spirally wound or coiled around longitudinal axis L. Moreover, while not previously discussed, in other non-illustrated forms elongate body 12 could be spirally wound or coiled around longitudinal axis L either more or less tightly than what is shown for the illustrated embodiment.

Elongate body 12 is generally radially expandable along longitudinal axis L as one or more objects, such as one or more devices, implants, or instruments, are engaged with and moved through inner channel 22 such that elongate body 12 is uncoiled relative to longitudinal axis L and inner channel 22 is expanded from the unexpanded configuration. Elongate body 12 can be configured to maintain its expanded configuration when inner channel 22 is expanded from its unexpanded configuration upon displacement of the one or more objects from inner channel 22, although forms where elongate body 12 resiliently returns or is configured to only partially return inner channel 22 to its unexpanded configuration are also contemplated. In one form, elongate body 12 may be formed of a thin metal or polymer material. However, any biocompatible material, including but not limited to non-reinforced polymers, carbon-reinforced polymer composites, shape-memory alloys, titanium, titanium alloys, cobalt chrome alloys, stainless steel and others as well, may be used to form elongate body 12, although it should be appreciated that it may be necessary to alter various design aspects of elongate body 12 depending on the material used.

Figure 2:
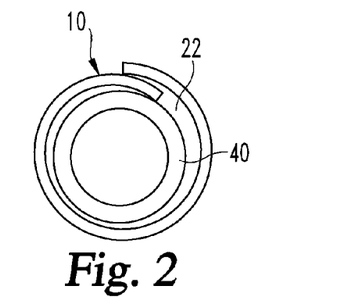
FIG. 2 is an end view of the sleeve of FIG. 1 positioned relative to a dilator.
Figure 3:
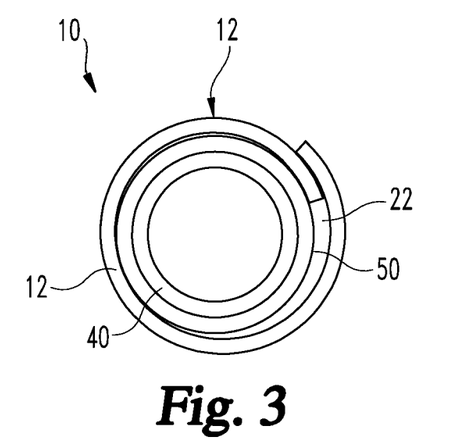
FIG. 3 is an end view of the sleeve and dilator illustrated in FIG. 2 with the inner channel of the sleeve in an expanded configuration to receive another dilator.

As illustrated in FIG. 2, positioning sleeve 10 at a surgical site with inner channel 22 in the unexpanded configuration can be accomplished by positioning sleeve 10 around a delivery dilator 40. Sleeve 10 extends around an outer surface of dilator 40 and has a cross-sectional size and shape orthogonal to longitudinal axis L that is slightly larger so that it is substantially the same as the cross-sectional size and shape of dilator 40 along all or a major portion of the length of body 12 of sleeve 10 between its proximal end 14 and distal end 16. Once sleeve 10 and dilator 40 have been inserted at the surgical site, inner channel 22 provides a space between dilator 40 and sleeve 10 to receive one or more additional dilators and/or a retractor while in its unexpanded configuration. Upon insertion of a larger object 50 within inner channel 22 during the surgical procedure, inner channel 22 will be expanded by object 50 to allow passage of object 50 in inner channel 22 and along the outer surface of dilator 40. More particularly, as illustrated in FIG. 3, elongate body 12 generally radially expands upon insertion of object 50 and provides an outer sleeve or sheath that prevents object 50 from contacting tissue along the surgical access portal. Similarly, additional larger objects can be placed around the last inserted object to radially expand elongate body 12 until the desired size of access portal to the surgical site is obtained. It should be appreciated that object 50 can be any type of device, implant or surgical instrument. Specific embodiments contemplate that object or objects 50 are dilators, cannulae, retractors, blades, and tubes, for example.

Figure 4:
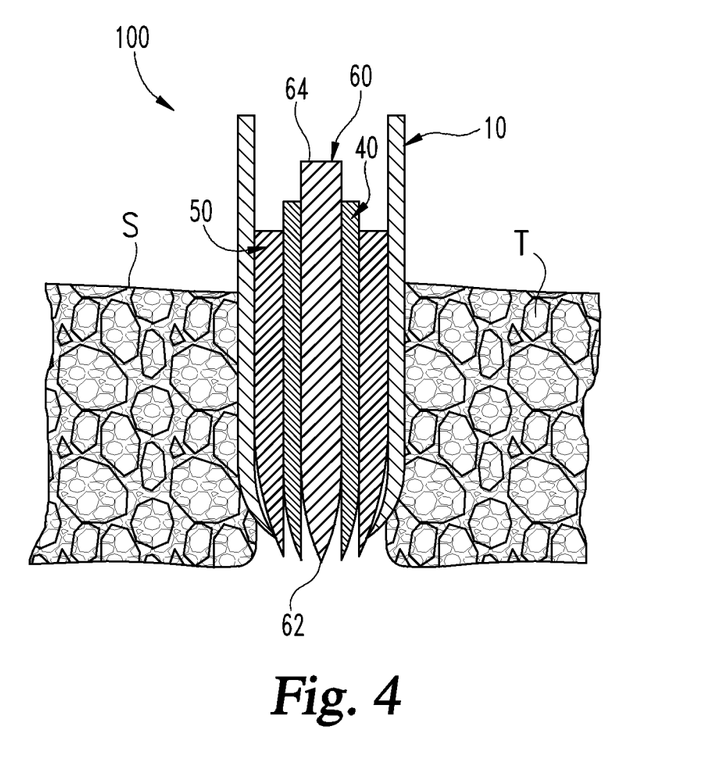
FIG. 4 is a longitudinal section view showing a dilator system and expandable sleeve.
Figure 5:
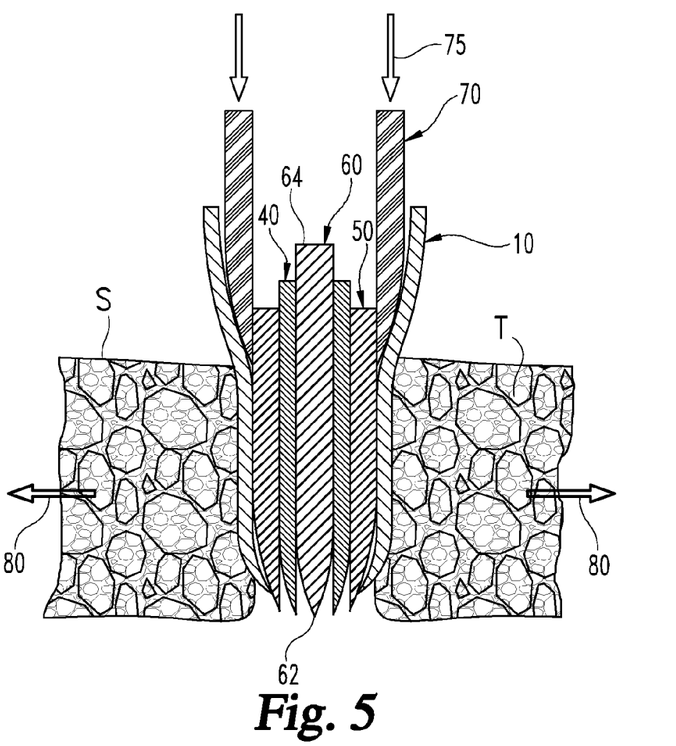
FIG. 5 is a longitudinal section view showing insertion of a larger dilator between the last inserted dilator and the expandable sleeve.
Figure 6:
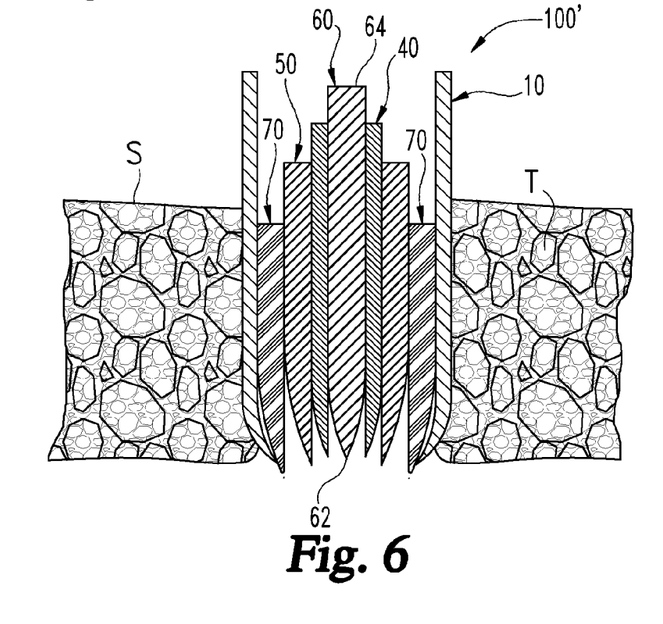
FIG. 6 is a longitudinal section view showing the larger dilator inserted between the expandable sleeve and the last inserted dilator.

Referring now to FIGS. 4-6, further details regarding sleeve 10 and its use will be provided. More particularly, as illustrated in the perspective view of FIG. 4, sleeve 10 is positioned through skin S and tissue T of a patient in an intermediate step of surgical procedure to provide an access portal to a surgical site at the distal end of sleeve 10. The instrument assembly 100 includes an elongate guidewire 60 positioned along the access path so that the distal end 62 of guidewire 60 is located at the surgical site and proximal end 64 of guidewire 60 extends from skin S so it is accessible by the surgeon. A first dilator 40 is positioned immediately adjacent to and around guidewire 60, and a second, larger dilator 50 is positioned around first dilator 40. Sleeve 10 is expanded to accommodate insertion of second dilator 50 in inner channel 22. It is contemplated that sleeve 10 could be delivered into the access portal during insertion of first dilator 40. Alternatively, sleeve 10 could be delivered with insertion of second dilator 50.

In order to further dilate the access portal, a third dilator 70 is inserted around second dilator 50 and in inner channel 22 of sleeve 10, as shown in FIG. 5. Sleeve 10 expands at its proximal end 14 to accommodate movement of third dilator 70 along the outer surface of second dilator 50 within inner channel 22. As third dilator 70 is distally advanced, as indicated by arrows 80, toward the distal end 16 of sleeve 10, radial expansion of sleeve 10 increases longitudinally with the longitudinal movement of third dilator 70. Sleeve 10 protects tissue along the access portal that would have been in contact with the distal end of third dilator 70 as it is moved longitudinally. When third dilator 70 is finally positioned as shown in FIG. 6, sleeve 10 provides an expanded protective sheath around instrument assembly 100' for insertion of another dilator or retractor along third dilator 70. Alternatively, third dilator 70 can remain implanted while the remaining dilators and guidewire are withdrawn so that third dilator 70 acts as a tubular retractor to maintain the access portal with sleeve 10 remaining in position around dilator 70.

Figure 7:
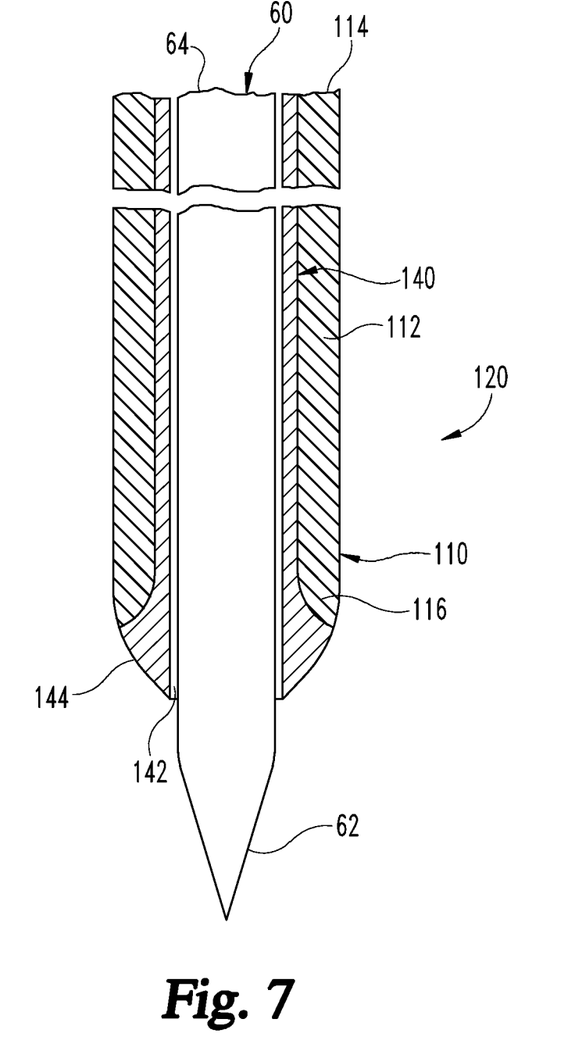
FIG. 7 is a longitudinal section view of another embodiment sleeve attached to a delivery dilator.

In FIG. 7 there is shown another embodiment dilator and expandable sleeve device 120. Device 120 includes a dilator 140 with an inner longitudinal passage 142 sized to receive, for example, guidewire 60. Other embodiments contemplate that passage 142 is sized for placement over one or more previously inserted dilators. Dilator 140 includes a distal end portion 144 that is flared radially outwardly relative to the remaining proximal portion of the elongated body of dilator 140. Sleeve 110 includes an elongated, expandable body 112 extending along the outer surface of dilator 140 from proximal end 114 to distal end 116. Distal end 116 is removably attached to at least distal end portion 114 so that sleeve 110 is carried by and inserted simultaneously with dilator 140 when device 120 is positioned over guidewire 60. When the next larger dilator or other object is positioned between sleeve 110 and dilator 140, sleeve 110 radially expands as the object is advanced longitudinally along dilator 140. When the object reaches distal end portion 144, sleeve 110 can detach from dilator 140 to allow passage of the object distally from sleeve 110.

Referring to FIGS. 8A-8E, there are shown various steps of one embodiment surgical technique employing the expandable sleeve discussed herein. In the illustrated method, a direct lateral approach of a spinal disc space D is shown between the L4 and L5 vertebrae. However, it should be understood that the expandable sleeve discussed herein has application in other surgical approaches to a spinal disc space D, and to other locations along the spinal column or within the patient. One examples of a direct-lateral technique for interbody fusion using sequential dilators and a retractor is discussed in the manual entitled "Direct Lateral Interbody Fusion DLIF Surgical Technique" ©2009 by Medtronic Sofamor Danek USA, Inc. which is incorporated herein by reference in its entirety.

Figure 8A:
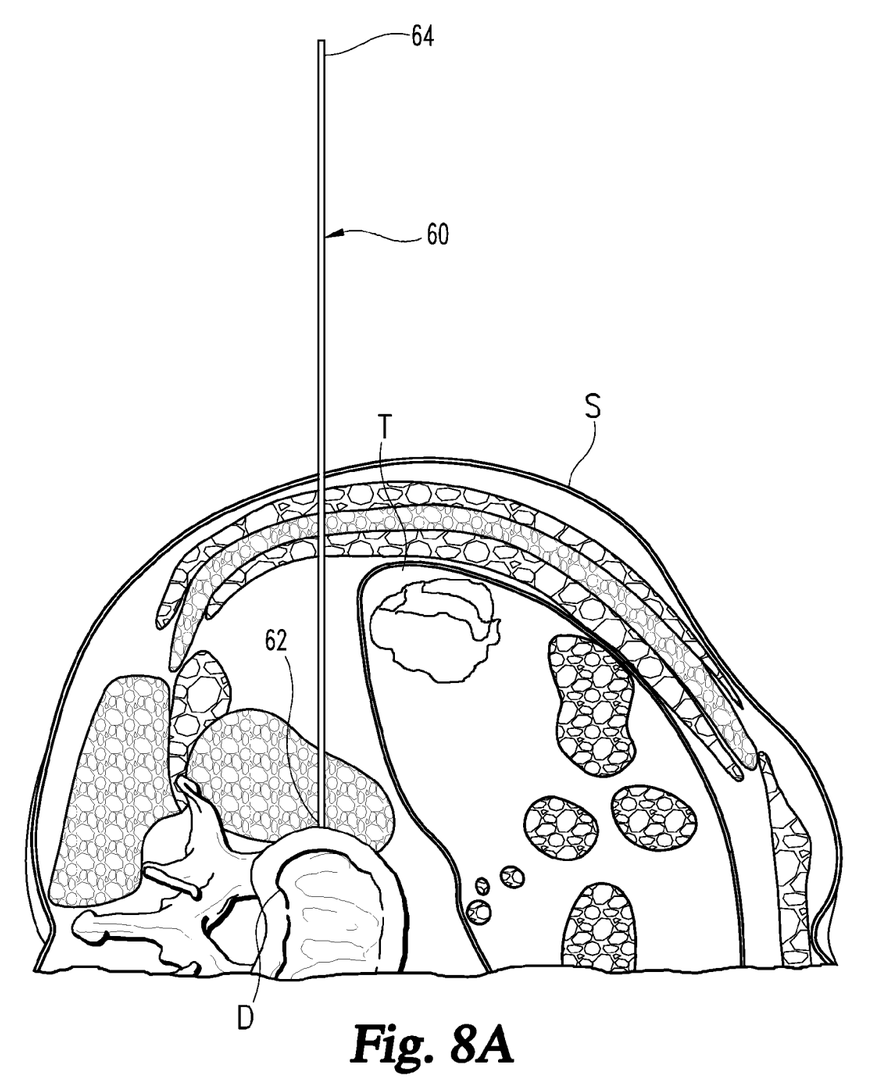
FIGS. 8A-8E show various steps of a surgical method using an expandable sleeve to protect tissue during insertion of dilators and retractors into the patient to form an access port to a spinal disc space.
Figure 8B:
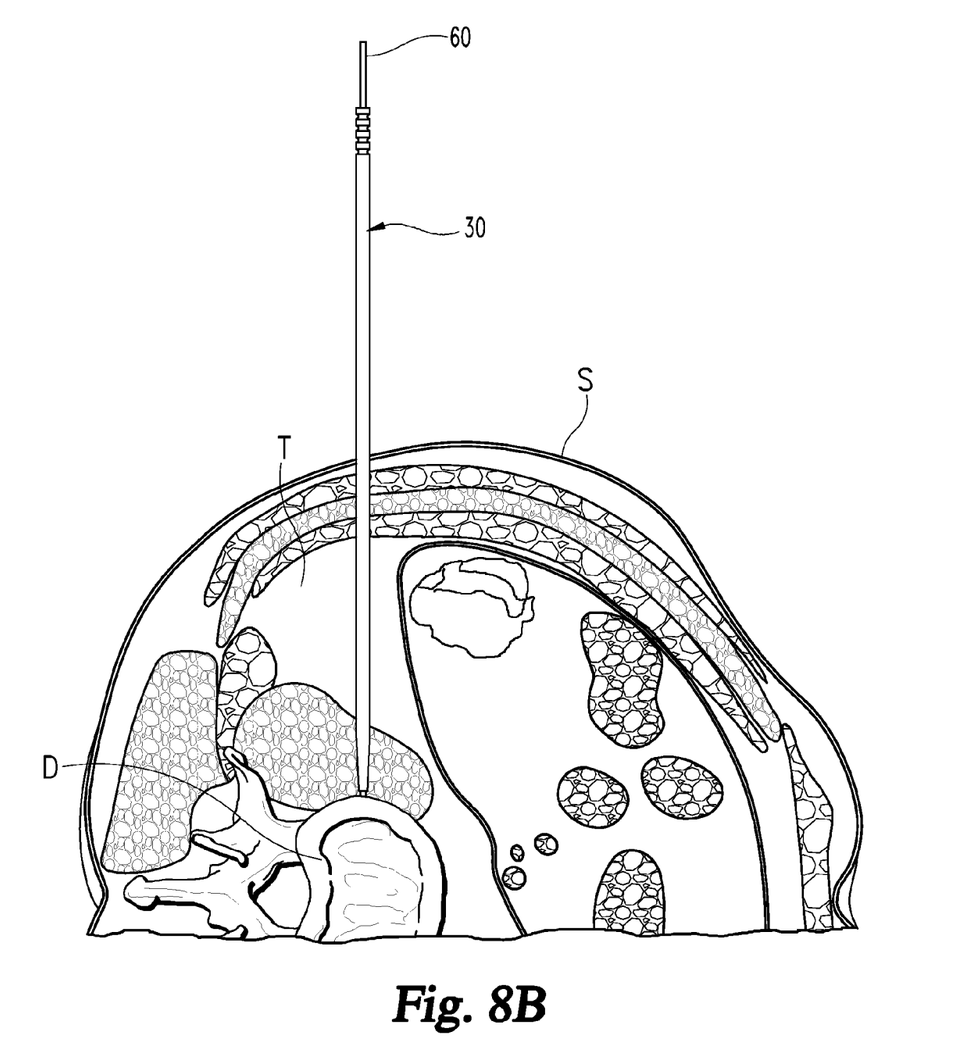
Figure 8C:
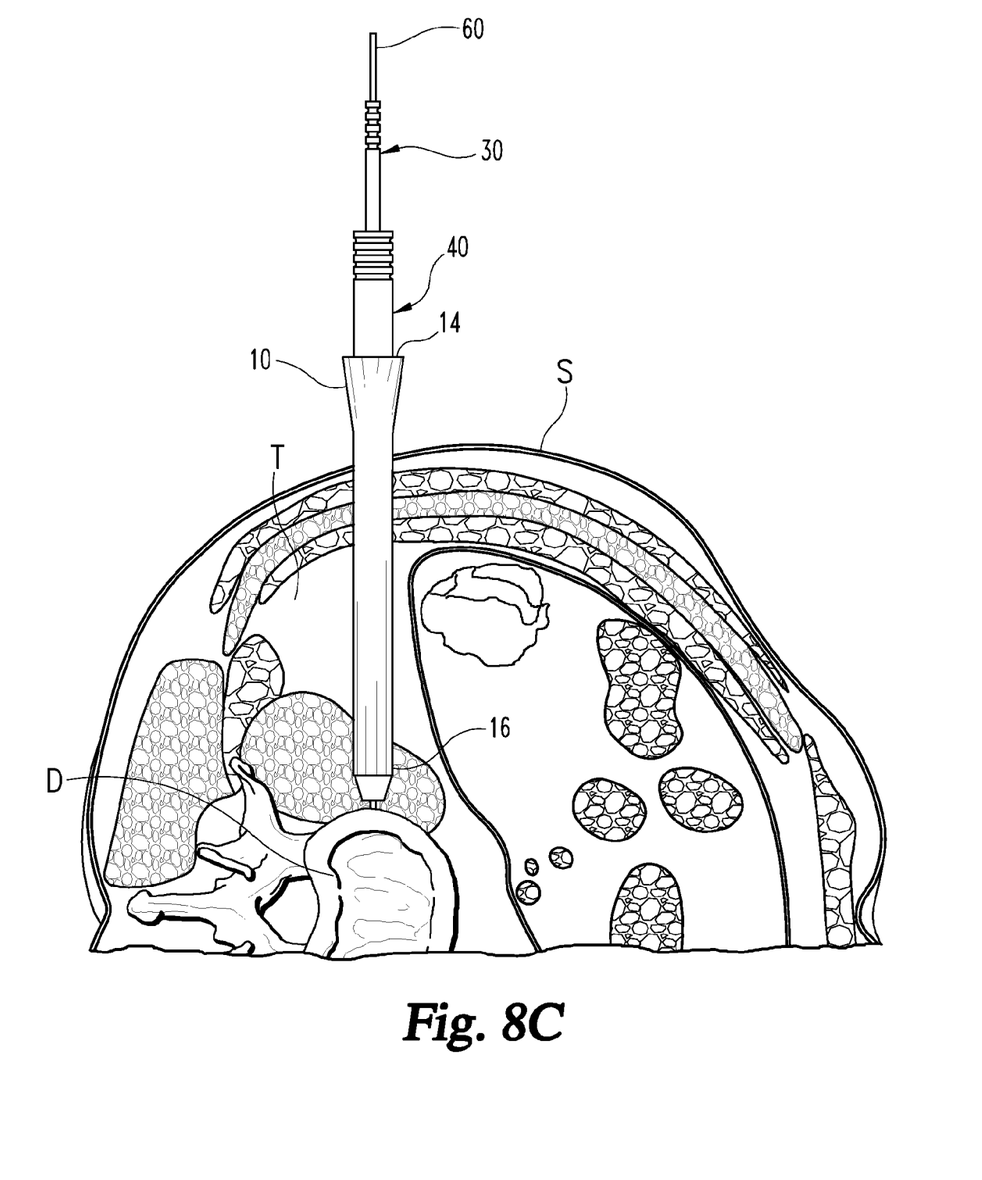

In FIG. 8A, guidewire 60 is inserted through skin S and tissue T of the patient to locate distal end 62 in or adjacent to disc space D. Guidewire 60 is oriented in a direct-lateral approach so that it is orthogonal or substantially orthogonal to the sagittal plane of the spinal column. Proximal end 64 extends proximally of skin S sufficiently to receive one or more dilators thereover. For example, FIG. 8B shows a first dilator 30 positioned over guidewire 60 and advanced therealong through skin S and tissue T to locate its distal end adjacent to disc space D. In FIG. 8C, a second, delivery dilator 40 with sleeve 10 positioned therearound is advanced along first dilator 40 and delivers sleeve 10 into the access portal. In the illustrated embodiment, the proximal end 14 of sleeve 10 is flared outwardly from dilator 50 proximally of skin S. Distal end 16 of sleeve 10 is located slightly offset in a proximal direction from disc space D.

Figure 8D:
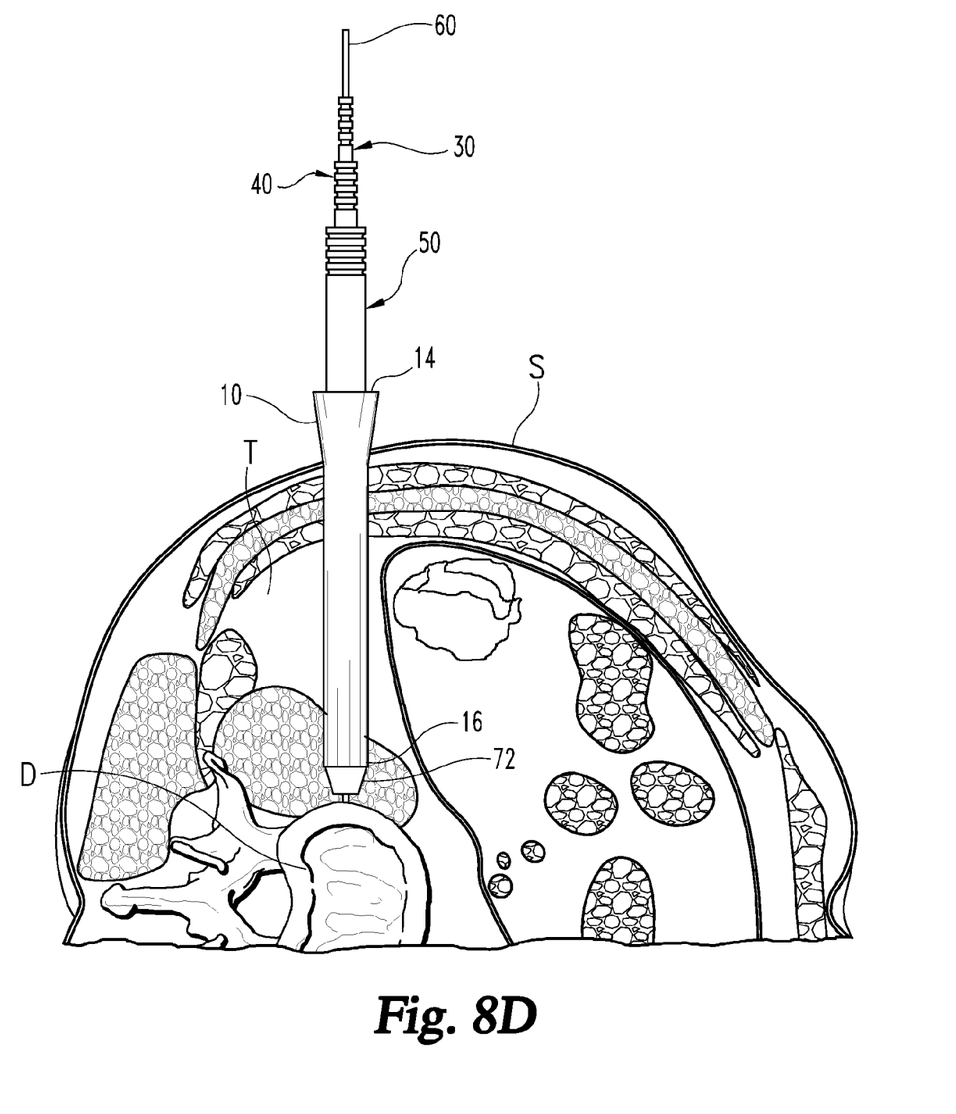
Figure 8E:
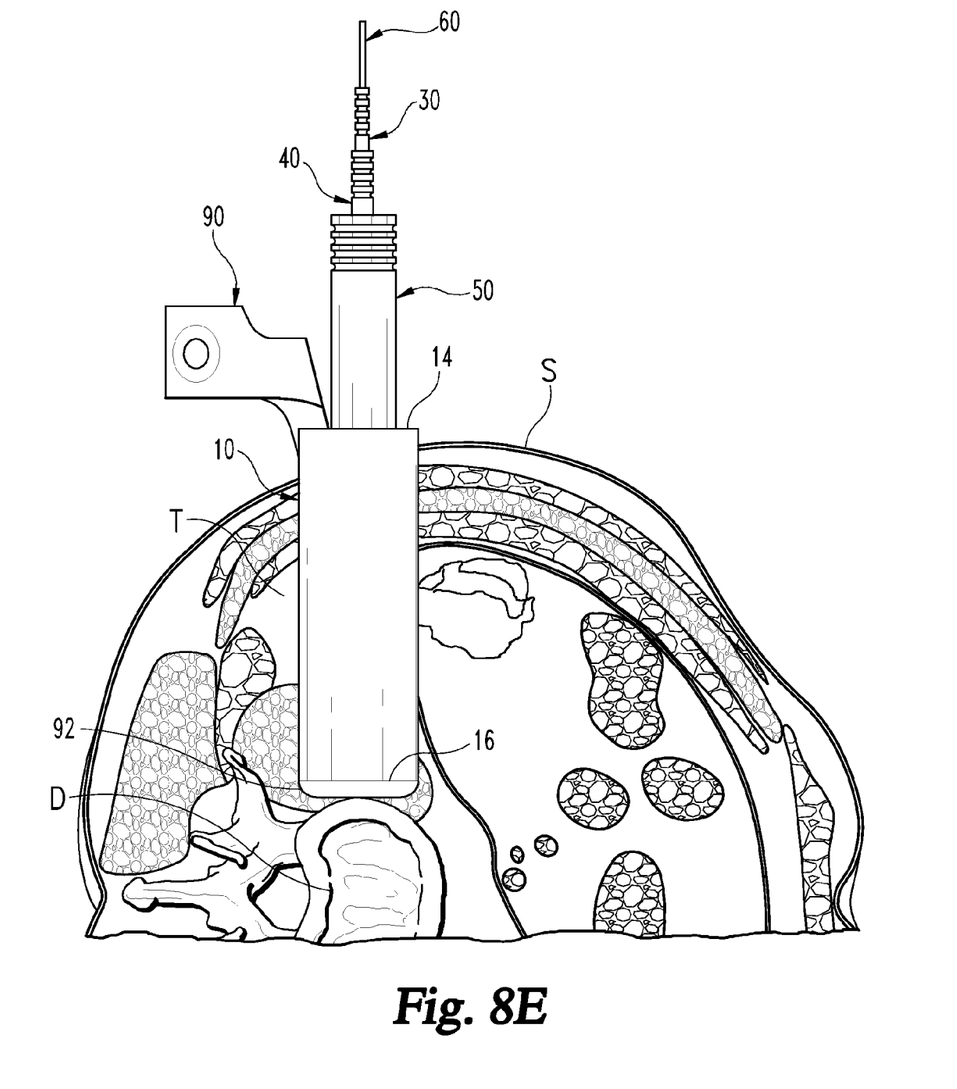

In FIG. 8D an object 50 such as a third dilator is positioned in the proximal, outwardly flared end opening of sleeve 10 between dilator 50 and sleeve 10. Sleeve 10 expands radially along its length to accommodate placement of third dilator 50 therein. In FIG. 8E, a retractor 90 is positioned in inner channel 22 of sleeve 10 between sleeve 10 and third dilator 70. Retractor 90 is advanced longitudinally to position its distal end 92 adjacent to disc space D near or in contact with the vertebrae on each side of disc space D. When retractor 90 is finally positioned, the dilators and guidewire are removed from the access port so that the surgeon has an unobstructed passage to disc space D. Sleeve 10 remains in position around retractor 90 as a sheath to prevent tissue encroachment into the access port maintained by retractor 90. This sheath can be particularly usefully if retractor 90 is comprised or two or more blades or segments. It should understood, however, that retractor 90 can be a unitary tube or cannula.

Figures 9, 10, 11, 12:
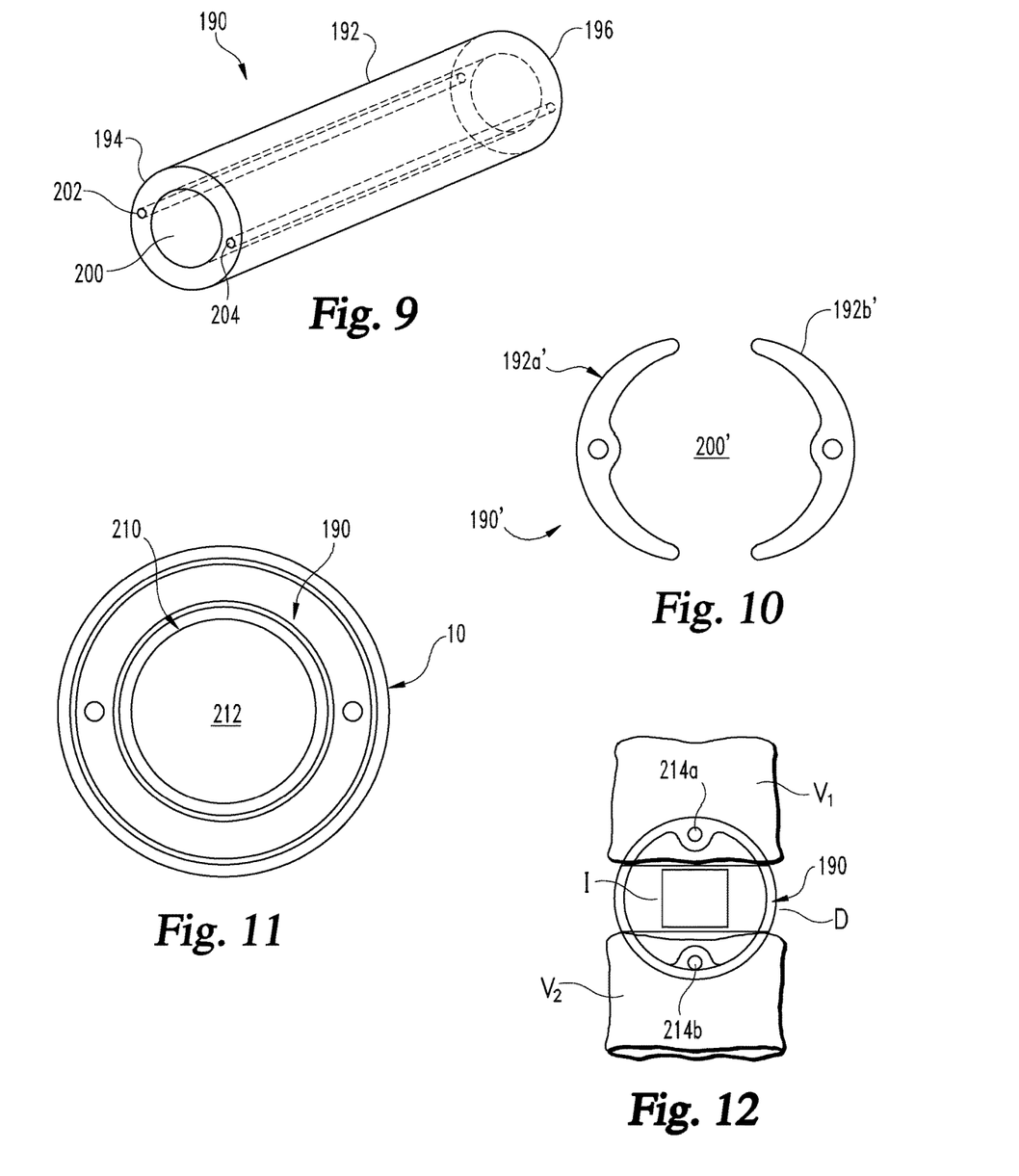
FIG. 9 is a perspective view of an embodiment of a retractor for maintaining an access portal to a surgical site during surgery.
FIG. 10 is an end view of another embodiment of the retractor of FIG. 9.
FIG. 11 is an end view of the retractor of FIG. 9 positioned around a support member and within the inner channel of an expandable sleeve.
FIG. 12 is a diagrammatic view showing the retractor and sleeve engaged to vertebral bodies to deliver an implant to a disc space.

Referring now to FIG. 9, there is shown another embodiment of a retractor 90 designated as retractor 190. Retractor 190 includes an elongated body 192 extending between a proximal end 194 and an opposite distal end 196. Body 192 defines a working channel 200 extending between and opening and proximal and distal ends 194, 196. Body 192 also defines first and second pin channels 202, 204 in a wall of body 192 that extend between and open at proximal and distal ends 194, 196. Elongate body 192 generally includes a length between proximal end 194 and distal end 196 that facilitates positioning of proximal end 194 above the skin of a patient when distal end 196 is positioned adjacent to the targeted surgical site. In addition, distal end 196 can be beveled to facilitate insertion in an incision, although non-beveled ends are also contemplated.

In a further embodiment of retractor 190 shown in FIG. 10 and designated as retractor 190', body 192 includes a pair of elongate members 192a', 192b' having a semi-circular cross-section and cooperate to form an expandable working channel 200' having a generally circular cross-section when elongate members 192a', 192b' are placed adjacent one another and working channel 200' is in an unexpanded configuration. Other cross-sectional shapes are also contemplated for elongate body 192 and/or first and second elongate members 192a', 192b', such as, for example, any open sided polygonal shape including but not limited to triangular, rectangular, hexagonal or octagonal shapes, curved shapes, or combined curved/polygonal shapes. Similarly, it should be appreciated that working channels 200, 200' can have a different cross-sectional shape. Working channels 200, 200' extend between and open at the proximal and distal ends of the retractor, and can be generally uniformly sized and shaped from the proximal end to the distal end, although forms where the size and/or shape of the working channel vary along the length of the retractor are also possible. In addition, embodiments where the retractor includes three or more elongate members defining the working channel are contemplated.

The working channel of retractors 190, 190' can have a size in the insertion configuration that allows access to the surgical site in the patient's body to perform one or more steps of the surgical procedure. However, it may be desirable during surgery to provide greater access to the surgical site in the patient's body beyond what is provided through the working channel in its unexpanded insertion configuration. Similarly, after insertion into the patient, working channel defined by retractor 190' can be enlarged by separating elongate members 192a', 192b' from one another along to expand the working channel along all or a portion of its length. When elongate members 192a', 192b' are separated from one another, the working channel can have a cylindrical, conical, or tapered shape with, for example, a cross-section that is oval, elliptical, circular, curved, polygonal, or combined polygonal/curved in shape. In addition, with sleeve 10 extending around elongate members 192a', 192b' of retractor 190', sleeve 10 assists in maintaining tissue out the working channel as it is expanded and protects the adjacent tissue as the retractor is manipulated in the tissue of the patient.

Retractors 190, 190' can be provided with sufficient rigidity between their proximal and distal ends to separate and maintain separation of tissue when tissue is retracted by the retractor. For example, the body or bodies of the retractor can include a thickness which provides sufficient rigidity to resist bending or bowing under the forces exerted on it by the retracted tissue. Furthermore, it is contemplated that bodies of the retractors can be made from any biocompatible material, including but not limited to non-reinforced polymers, carbon-reinforced polymer composites, shape-memory alloys, titanium, titanium alloys, cobalt chrome alloys, stainless steel, PEEK, and others as well.

As illustrated in FIG. 11 with respect to retractor 190, it being understood that retractor 190' could also be similarly arranged, a support member 210 can be positioned in working channel 200 of retractor 190 and sleeve 10 can be positioned around the outer surface of retractor 190 so that support member 210 and sleeve 10 extend substantially between the proximal and distal ends of the retractor. A passage 212 in support member 210 can be provided for embodiments in which support member 210 is a dilator to be positioned over one or more previously inserted dilators. Retractor 190 can be releasably attached to support member 210 so that the retractor and support member can be delivered together into the patient in the inner channel 22 of sleeve 10. Sleeve 10 can be provided with a length between proximal end 14 and distal end 16 that substantially corresponds to the length of retractor 190 between proximal end 194 and distal end 196; however, it is contemplated that at least the distal end of retractor 190 protrudes distally from the distal end of sleeve 10 and the proximal end of retractor 190 protrude proximally from the proximal end 16 of sleeve 10 such as shown with respect to retractor 90 and sleeve 10 in FIG. 8E. In addition, while not previously discussed, the retractors herein can also be provided with a brace or other support arm adjacent to their proximal ends which can be coupled with one or more operating room support structures. Examples of operating room support structures include, without limitation, support arms, braces and other linkage members which are coupled to an operating table or bed and movable to position the retractor relative to a surgical site of the patient. Additionally or alternatively, medical tape or other suitable adhesive materials can be attached to the retractor and/or sleeve 10 and skin or other anatomical features of the patient near the surgical site in order to stabilize the retractor during the surgical procedure.

The retractor and support member combination can be delivered simultaneously into the access portal of the patient by positioning support member 190 over a dilator, such as dilator 50 in FIG. 8D, and into inner channel 22 of sleeve 10. As the retractor and support member combination 190/210 are distally advanced into the patient along dilator 50, sleeve 10 expands progressively outwardly in a longitudinal direction. When the retractor is in its desired location, the dilators and support member can be removed from the access portal to leave the retractor with sleeve 10 positioned therearound in place in the access portal into the patient, such as shown in FIG. 12. The retractor can be secured in position with bone pins, such as elongate bone pins 214a, 214b positioned in pin channels 202, 204 of retractor 190, secure retractor 190 in position relative to respective ones of the vertebrae V1, V2. An implant I can then be delivered through working channel 200 to the disc space D for implantation in the patient. The retractor and sleeve combination is then withdrawn from the patient. It is contemplate that the retractor and sleeve can then be disposed of. However, applications where one or both of the retractor and sleeve are sterilized for re-use is not precluded.

Sleeve 10 is generally formed of a flexible, pliable or elastic material that is stretchable from an initial configuration upon the application of sufficient force. Sleeve 10 may resiliently return toward its initial configuration upon release of the force, or be permanently deformable to maintain its expanded shape. In one form, sleeve 10 can be omni-directionally stretchable, although forms are also contemplated where the ability of sleeve 10 to stretch in one or more directions is limited. While not being limited to any particular form, non-limiting examples of materials from which sleeve 10 may be formed include fabrics or polymers, including elastomers such as rubber and latex or other similar non-allergenic polymers, although it should be appreciated that the use any biocompatible material exhibiting the properties discussed above in this paragraph is also contemplated In one or more non-illustrated forms, it should be appreciated that sleeve 10 can be attached or affixed to one or more portions of the exterior surfaces of the dilator which is to deliver it to the surgical site, such as dilator 40 shown in FIG. 2 or dilator 140 shown in FIG. 7. In one particular form, sleeve 10 could be glued or otherwise adhered to the dilator or delivery member, although other means for affixing sleeve 10 are also possible. Among other things, it is contemplated that affixing sleeve 10 to one or more portions of the delivery member in this manner will assist in delivery of sleeve 10 to the surgical site in the patient so that the substantially the entire length of the access portal into the patient is protected by sleeve 10 during subsequent insertion of dilators and/or retractors.

Upon initial insertion of a device into inner channel 22 of sleeve 10, it is contemplated that sleeve 10 may only expand adjacent to proximal end 14 of elongate body 12 where the device is located, although expansion of inner channel 22 along its length from proximal end 14 to distal end 16 of body 12 is also possible. As the device is distally advanced through inner channel 22, sleeve 10 progressively expands in a longitudinal direction along its length until the device exits inner channel 22 from distal end 16 of elongate body 12. In one form, it is contemplated that inner channel 22 can be uniformly sized and shaped when it is expanded by the device, although forms where inner channel 22 is non-uniformly sized and shaped between proximal end 14 and distal end 16 when the device is positioned therein are also contemplated.

While not previously discussed, sleeve 10 can be arranged such that as it is expanded, expansion of inner channel 22 is maintained, either selectively or otherwise. For example, in one form a mechanism such as a locking hinge is positioned between adjacent portions of sleeve 10 and allows their displacement away from one another but prevents their return toward one another once a threshold separation distance therebetween is achieved. In another form, overlapping edges of a coiled sleeve 10, such as shown in FIG. 1, include interlocking teeth or a ratcheting arrangement to lock sleeve 10 in an expanded configuration. Still, it should be appreciated that other alternative locking mechanisms are also contemplated, including those that are selectively releasable from their locked state in order to allow the return sleeve 10 to an unexpanded state.

As indicated above, certain devices or instruments to be used or positioned at the surgical site are inserted through inner channel 22 and expand sleeve 10 outwardly from longitudinal axis L as they are inserted and advanced therethrough. It is contemplated that sleeve 10 expands radially outwardly from longitudinal axis L, although embodiments in which sleeve 10 expands uni-directionally, bi-directionally, or non-uniformly about longitudinal axis L are contemplated.

While not previously discussed, it should be appreciated that the devices or instruments that are positioned through inner channel 22 and result in the expansion of sleeve 10 from its unexpanded configuration could be provided with leading and/or trailing ends that are tapered, convexly rounded, conically shaped or otherwise suitably configured to facilitate initial engagement with the internal surfaces of body 12 that extend around inner channel 22. Additionally or alternatively, the internal surface of inner channel 22 adjacent one or both of proximal end 14 and distal end 16 may be provided with a chamfered or correspondingly tapered section that interacts with the leading and/or trailing ends of the device or instrument to facilitate engagement with inner channel 22. In addition, the inner surface of body 12 along inner channel 22 can be coated with a lubricant to facilitate movement of the device along the inner surface.

The outer surface of sleeve 10 opposite inner channel 22 can be coated with an anti-microbial agent or other pharmaceutical to reduce the potential for infection and promote healing of tissue in contact with sleeve 10 after the surgery.

In other non-illustrated forms of sleeve 10, it can include non-circular cross-sectional shapes, non-limiting examples of which include triangular, rectangular, hexagonal or octagonal shapes, curved shapes, or combined curved/polygonal shapes. It should be appreciated that disc space D can be accessed from any of an anterior, posterior, anterolateral, postero-lateral or lateral approach. It should also be appreciated that insertion and positioning of sleeve 10 without guidewires and dilators is also possible and contemplated in connection with the use of sleeve 10. Furthermore, it is contemplated sleeve 10 can be positioned directly through the skin and tissue of a patient to a location adjacent a surgical site.

Alternative configurations and uses of the systems and methods described herein are also contemplated. For example, in one form, one or more additional retractors and sleeves could be positioned at one or more other vertebral levels of the spinal column in order to perform a surgical procedure across multiple levels of the spinal column. In addition, the systems and methods described herein may also be used in surgical procedures involving animals, or in demonstrations for training, education, marketing, sales and/or advertising purposes. In addition, the systems and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A surgical system, comprising:
  a dilator extending along a longitudinal axis between a proximal end and a distal end, the dilator being tapered from the proximal end to the distal end, the dilator including a passage extending between said ends;
  a sleeve extending continuously between opposite first and second side surfaces, said sleeve having a length extending along said longitudinal axis from a proximal end to a distal end of said sleeve, said proximal and distal ends of said sleeve each extending continuously between said side surfaces, said sleeve defining an inner channel between said proximal end and said distal end of said sleeve, said inner channel comprising a first opening at said proximal end of said sleeve and a second opening at said distal end of said sleeve, said sleeve being at least partially coiled around said longitudinal axis from said proximal end to said distal end of said sleeve such that said first side surface overlaps said second side surface, said dilator being positioned in said inner channel, wherein said sleeve is expandable from a first, unexpanded configuration, wherein in said first configuration said inner channel defines a cross-sectional size and shape orthogonal to said longitudinal axis that is substantially the same as a cross-sectional size and shape as said dilator along a major portion of said length of said sleeve; and a device in said inner channel between said sleeve and said dilator such that an inner surface of the device directly engages an outer surface of the dilator, wherein as said device is inserted said inner channel outwardly expands from said first configuration to a second, expanded configuration as said device is moved longitudinally along said dilator from said proximal end to said distal end of said dilator, said sleeve being configured to be maintained in the second, expanded configuration upon removal of said device from said inner channel, wherein a proximal end surface of said device is positioned between said proximal and distal ends of said sleeve and an opposite distal tip of said device extends through said second opening when said sleeve is in said second configuration.

2. The system of claim 1, wherein said device includes at least one retractor having an elongated blade extending between a distal end and a proximal end, said elongated blade defining a working channel along an inner surface of said blade, said elongated blade further defining at least one pin bore between said inner surface and an opposite outer surface of said elongated blade that extends from said distal end to said proximal end, and further comprising an elongated pin in said pin bore for engaging said at least one retractor blade to bony structure.

3. The system of claim 2, wherein said at least one elongated blade of said retractor includes a second elongated blade extending between a distal end and a proximal end, said second elongated blade defining with the other of said elongated blades said working channel between inner surfaces of said elongated blades.

4. The system of claim 1, wherein said inner channel of said sleeve flares radially outwardly toward said proximal end of said sleeve.

5. The system of claim 1, wherein said sleeve stretches to expand outwardly.

6. The system of claim 1, wherein said device is a second dilator including an elongate body extending along a longitudinal axis between a proximal end and a distal end and including a passage extending between and opening at said proximal end and said distal end of said second dilator, said passage being sized to receive said dilator therein.

7. The system of claim 1, wherein said device is a retractor including an elongate blade extending along a longitudinal axis between a proximal end and a distal end, wherein said retractor maintains separation of tissue when tissue is retracted by said retractor.

8. The system of claim 1, wherein said sleeve is at least partially coiled around said longitudinal axis from said proximal end to said distal end of said elongate body such that said sleeve uncoils as it expands.

9. The system of claim 1, wherein said dilator includes a distal end portion at said distal end that is flared radially outwardly and said sleeve is releasably attached to said flared distal end portion of said dilator.

10. The system of claim 1, wherein said device comprises at least two dilators of increasing size so that a first of said at least two dilators is positionable around a second of said at least two dilators, only one of said at least two dilators being configured to extend through said second opening.

11. The system of claim 1, further comprising a guide wire positionable through said passage of said dilator.

12. The system of claim 1, wherein said second configuration substantially corresponds in cross-sectional size and shape to a cross-sectional size of at least a portion of said device.

13. The system of claim 1, wherein said sleeve is formed of a thin metal.

14. The system of claim 1, wherein said sleeve is formed of a shape-memory alloy.

15. The system of claim 1, wherein said inner channel is generally uniformly sized and shaped between said proximal and distal ends of said elongate body when said sleeve is in said first configuration.

16. The system of claim 1, wherein said device is removable relative to said dilator such that said dilator remains within said inner channel when said device is removed from said inner channel.

17. A method, comprising:
providing the surgical system recited in claim 1;
positioning the dilator and the sleeve simultaneously at a location adjacent to a surgical site with the sleeve in the first, unexpanded configuration; and
inserting the device around the dilator and into the inner channel of the sleeve and expanding the sleeve as the device is distally advanced through the inner channel toward the surgical site.

18. The method of claim 17, wherein the expanding is initiated upon engaging the device with an inner surface of the sleeve at the proximal end of the elongate body.

19. A surgical system, comprising:
a dilator extending between a first end and a second end;
a sleeve extending along a longitudinal axis between a proximal end and a distal end, an inner surface of the sleeve defining an inner channel that extends between the proximal and distal ends and includes a first opening at the proximal end and a second opening at the distal end, the sleeve being at least partially coiled around the longitudinal axis from the proximal end to the distal end, the dilator being positioned in the inner channel, wherein the sleeve is expandable from a first, unexpanded configuration in which the inner channel has a cross-sectional size and shape orthogonal to the longitudinal axis that is substantially the same as a cross-sectional size and shape of the dilator; and
a device positioned in the inner channel between the sleeve and the dilator such that an inner surface of the device directly engages an outer surface of the dilator, wherein as the device is inserted, the inner channel outwardly expands from the first configuration to a second, expanded configuration as the device is moved longitudinally along the dilator from the first end to the second end, the sleeve being configured to be maintained in the second, expanded configuration upon removal of the device from the inner channel, wherein a proximal end surface of the device is positioned between the proximal and distal ends and an opposite distal tip of the device extends through the second opening when the sleeve is in the second configuration.

20. A surgical system, comprising:

a dilator extending between a first end and a second end;

a sleeve extending along a longitudinal axis between a proximal end and a distal end, an inner surface of the sleeve defining an inner channel that extends between the ends and includes openings at the proximal end and the distal end, the sleeve being at least partially coiled around the longitudinal axis from the proximal end to the distal end, the dilator being positioned in the inner channel, wherein the sleeve is expandable from a first, unexpanded configuration in which the inner channel has a cross-sectional size and shape orthogonal to the longitudinal axis that is substantially the same as a cross-sectional size and shape of the dilator; and a device positioned in the inner channel between the sleeve and the dilator such that an inner surface of the device directly engages an outer surface of the dilator, wherein as the device is inserted, the inner channel outwardly expands from the first configuration to a second, expanded configuration as the device is moved longitudinally along the dilator from the first end to the second end, the sleeve being configured to only partially return to the first, unexpanded configuration upon removal of the device from the inner channel, wherein a distal tip of the device extends through the opening in the distal end when the sleeve is in the second configuration.

* * * * *

UNITED STATES PATENT AND TRADEMARK OFFICE
CERTIFICATE OF CORRECTION

PATENT NO. : 9,795,771 B2  
APPLICATION NO. : 12/907199  
DATED : October 24, 2017  
INVENTOR(S) : Trieu et al.

Page 1 of 1

It is certified that error appears in the above-identified patent and that said Letters Patent is hereby corrected as shown below:

In the Specification

In Column 5, Line 67, delete "distal end portion 114" and insert -- distal end portion 144 --, therefor.

In Column 8, Line 13, delete "proximal end 16" and insert -- proximal end 14 --, therefor.

Signed and Sealed this  
Second Day of January, 2018

Joseph Matal  
*Performing the Functions and Duties of the*  
*Under Secretary of Commerce for Intellectual Property and*  
*Director of the United States Patent and Trademark Office*